United States Patent [19]

Thys-Jacobs

[11] Patent Number: 5,443,850

[45] Date of Patent: Aug. 22, 1995

[54] METHOD FOR TREATING SYMPTOMS ASSOCIATED WITH VASCULAR HEADACHES BY ADMINISTERING A COMBINATION OF CALCIUM AND VITAMIN D

[76] Inventor: Susan Thys-Jacobs, 135 Hickory Grove Dr., Larchmont, N.Y. 10538

[21] Appl. No.: 203,259

[22] Filed: Mar. 1, 1994

Related U.S. Application Data

[63] Continuation-in-part of Ser. No. 59,682, May 10, 1993, which is a continuation-in-part of Ser. No. 945,319, Sep. 15, 1992, abandoned.

[51] Int. Cl.$^6$ .................... A61K 33/06; A61K 33/10; A61K 31/59
[52] U.S. Cl. .................... 424/682; 424/687; 514/167; 552/653
[58] Field of Search .................... 514/167; 552/653; 424/687, 682

[56] References Cited

U.S. PATENT DOCUMENTS

| | | | |
|---|---|---|---|
| 4,501,738 | 2/1985 | Yamato et al. | 514/167 |
| 4,540,584 | 9/1985 | Someya | 424/156 |
| 4,806,354 | 2/1989 | Green | 424/154 |
| 4,812,303 | 3/1989 | Iorio | 424/44 |
| 4,946,679 | 8/1990 | Thys-Jacobs | 424/682 |

OTHER PUBLICATIONS

Stedman's Medical Dictionary, 24th Edition, Williams & Wilkins. 1983, p. 1536.

Bohr D., "Vascular Smooth Muscle; Dual Effect of Calcium", 1963, 19:597–599.

Cole et al., "Migraine With Vasospasm And Delayed Intracerebral Hemorrhage", *Arch Neurol,* 1990, 47:53–56.

Diamond et al., *The Practicing Physician's Approach to Headache,* Baltimore, The Williams & Wilkins Co., 1978, 51–66.

Edelson, R. N., "Menstrual Migraine and Other Hormonal Aspects of Migraine", *Headache,* 1985, 25:376–379.

Ferin et al., "The Menstrual Cycle Physiology, Reproductive Disorders, and Infertility", *Oxford Univ. Press,* 1993, 8:92–104; 15:198–246.

Francis et al. "Calcium Malabsorption In The Elderly: The Effect of Treatment With Oral 25-hydroxyvitamin D3", *European J.Clin. Invest.,* 1983, 13:391–396.

Heaney R., *Calcium, Bone Health and Osteoporosis In Bone and Mineral Research,* Elsevier Science Publishers., 1986, 255–301.

Humphrey et al., "Anti-Migraine Drugs In Development: Advances In Serotonin Receptor Pharmacology", *Headache,* 1990, 30:12–16.

International Headache Society. "Classification and Diagnostic Criteria for Headache Disorders, Cranial Neuralgias and Facial Pain", *Cephalagia,* 1988, 8 (suppl 7):19–22.

Linet et al., "Migraine Headache: Epidemiologic Perspectives", *Epidem. Rev.,* 1984, 6:107–39.

Peroutka S. J., "The Pharmacology of Current Anti-Migraine Drugs", *Headache,* 1990, 30:5–11.

Rasmussen, "Cellular Calcium Metabolism", *Ann Intern Med.,* 1983, 98:809–816.

Sanin et al., "Severe Diffuse Intracranial Vasospasm As A Cause Of Extensive Migranious Cerebral Infarction", *Cephalalgia,* 1993, 13:289–92.

Sargent et al., "A comparison of Naproxen Sodium to Propranolol Hydrochloride and a Placebo Control For (List continued on next page.)

*Primary Examiner*—Raymond Henley, III
*Assistant Examiner*—T. J. Criares
*Attorney, Agent, or Firm*—Pennie & Edmonds

[57] ABSTRACT

The present invention is directed to a method for treating symptoms associated with vascular headaches. The method comprises administering to an individual exhibiting symptoms associated with vascular headache symptomatology a therapeutically effective amount of a combination of calcium and vitamin D.

18 Claims, No Drawings

OTHER PUBLICATIONS

Health Care Utilization", *Cephalalgia,* 1993, 13:41–46.

Stewart et al., "Prevalence of Migraine Headache in the United States", *JAMA,* 1992, 267:64–9.

Thys–Jacobs et al., "Calcium Supplementation in Premenstrual Syndrome", *J. Gen. Intern. Med.,* 1989, 4:183–189.

Thys–Jacobs et al., "Vitamin D and Calcium Inadequacy in Women with Premenstrual Syndrome—Evidence of Reduced Bone Mass", Abstract presentation at the Endocrine Society, 1993, p. 309.

Welch, K.M.A., "Drug Therapy of Migraine", *The New England Journal of Medicine,* 1993, pp. 1476–1483.

The Prophylaxis of Migraine Headache", *Headache,* 1985, 25:320–324.

Solbach et al., "Headache: Migraine Associated With Menstruation", *Internal Medicine,* 1986; 7:93–103.

Spierings, EL, "Angiographic Changes Suggestive of Vasospasm in Migraine Complicated by Stroke", *Headache,* 1990, 30:727–8.

Strang et al., "Impact of Migraine In the United States: Data From the National Health Interview Survey", *Headache,* 1993, 33:29–35.

Stewart et al., "Migraine Headache: Epidemiology and

METHOD FOR TREATING SYMPTOMS ASSOCIATED WITH VASCULAR HEADACHES BY ADMINISTERING A COMBINATION OF CALCIUM AND VITAMIN D

This is a continuation-in-part, of application Ser. No. 08/059,682, filed May 10, 1993 pending which is a continuation-in-part of application Ser. No. 07/945,319, filed Sep. 15, 1992, now abandoned

BACKGROUND OF THE INVENTION

TECHNICAL FIELD

This invention relates to a method for reducing or relieving symptoms associated with vascular headaches, including migraine headaches, by administering to a person exhibiting vascular headache symptomatology a therapeutically effective amount of a combination of calcium and vitamin D.

BACKGROUND OF THE ART

Vascular headaches, including migraine headaches, are a common problem among Americans, migraines affecting approximately ten to twenty percent of the population, or 9–11 million Americans. Stewart et al., "Prevalence of Migraine Headache in the United States", *JAMA* 1992, 267:64–9; Ries, P. W., *Current Estimates from the National Health Interview Survey, United States,* 1984; *National Center for Health Statistics, Vital and Health Statistics,* Series 10, No. 156; *Department of Health and Human Services Publication* (PHS), 1986, 86–1584. Migraines appear to occur most often in people who are under 30 years of age, and women are two to three times more affected than are men. Stang et al., "Impact of Migraine In the United States: Data From the National Health Interview Survey" *Headache,* 1993, 33:29–35; Solbach et al., "Headache: Migraine Associated With Menstruation", *Internal Medicine,* 1986, 7:93–103. Eight to twenty-nine percent of women experience migraines during their lifetimes, while four to nineteen percent of men are so afflicted during their lives. Linet et al., "Migraine Headache: Epidemiologic Perspectives", *Epidem. Rev.,* 1984, 6:107–39. One authority cites that seventy percent of women who suffer with migraines report a significant proportion of attacks during the premenstrual period. Diamond et al., *The Practicing Physician's Approach to Headache,* Baltimore, The Williams & Wilkins Co., 1978, 51–66.

While migraines can vary in severity, duration, frequency and in expression, similar experiences have been reported for both males and females with regard to frequency and clinical manifestations. For example, in one epidemiological survey, 59% of females and 50% of male migraine sufferers experienced one or more attacks per month. Stewart et al., "Migraine Headache: Epidemiology and Health Care Utilization", *Cephalalqia,* 1993, 13:41–46.

Moreover, 25% of women and men migraineurs experience four or more severe attacks per month. Id. Furthermore, over 30% of migraine sufferers reported severe disability or the need for bed rest from the attacks. Attacks can be so disabling that work and everyday life are seriously affected.

Migraines are most often characterized by a hemicranial location (can be holocephalic as well) pulsating pain, light or sound sensitivity, and nausea or vomiting. The protean manifestations of migraines have frustrated the study, measurement and alleviation of this disorder. Recent consensus on classification by the International Headache Society has provided a major step in the standardization of specific diagnostic criteria for migraines. "International Headache Society, Classification and Diagnostic Criteria for Headache Disorders, Cranial Neuralgias and Facial Pain", *Cephalalgia,* 1988, 8(suppl. 7):19–22.

Migraines appear to be a cyclic vascular phenomena. Multiple theories of the pathophysiology of this vasomotor disturbance have been reported. The most popular focus on vasodilatation of the cerebral vessels, carotid arteriovenous shunting, and inflammation of the vasculature. Currently, overwhelming evidence points to some involvement of the serotonin neurotransmitter, 5 hydroxytryptamine, in the genesis of migraine headaches. Humphrey et al., "Anti-Migraine Drugs In Development: Advances In Serotonin Receptor Pharmacology", *Headache,* 1990, 30:12–16. There is good evidence that migraine represents a serotonin deficient state. The serotoninergic (5HT) system is complex involving 3 families and their subtypes, and has been implicated in multiple site actions such as intracranial vasoconstriction, smooth muscle relaxation, platelet aggregation and neuronal depolarization. Id.

To date, the acute and prophylactic pharmacological approaches to migraine have involved, with the exception of aspirin and similar agents, an agonist or antagonist effect on the various 5 hydroxytryptamine family subtypes. Drugs presently used for acute migraine attacks include aspirin, ergot preparations and sumatriptan. Peroutka S. J., "The Pharmacology of Current Anti-Migraine Drugs", Headache, 1990, 30:5–11. Clinically available prophylactic agents are beta-adrenergic drugs, antidepressants, calcium channel blockers and 5 hydroxytryptamine antagonists as methysergide.

In 1989, a randomized, crossover trial explored the effect of calcium supplementation in women with premenstrual syndrome (PMS). Thys-Jacobs et al., "Calcium Supplementation in Premenstrual Syndrome", *J. Gen. Intern. Med.,* 1989, 4:183–189. In this trial, elemental calcium was noted to have a major benefit in the reduction of premenstrual symptomatology, including relief from migraine headaches. The menstrual migraine is similar to the migraine, but has been temporally defined within the days of the menstrual period. Because the menstrual cycle has been observed to influence not only the occurrence of PMS but the frequency of headache attacks in premenopausal migraineurs, a possible association between premenstrual syndrome and migraine has been suggested. Sargent et al., "A comparison of Naproxen Sodium to Propranolol Hydrochloride and a Placebo Control For The Prophylaxis of Migraine Headache", *Headache,* 1985, 25:320–324.

Furthermore, in parent application Ser. No. 08/059,682, Thys-Jacobs discloses and claims a method for significantly reducing vascular headaches, including migraine headaches, associated with PMS.

However, there still exists a need for therapy that provides a reduction or relief of symptoms associated with migraines regardless of the gender or reproductive status of the individual experiencing such symptomatology.

SUMMARY OF THE INVENTION

An object of the present invention is to significantly reduce or relieve symptoms associated with migraine headaches in an individual exhibiting such symptoms.

The present invention is directed to a method for significantly reducing symptoms associated with vascular headaches, including migraine headaches. A therapeutically effective amount of a combination of calcium and vitamin D is administered to an individual exhibiting symptomatology associated with vascular headaches, including migraines.

DETAILED DESCRIPTION OF THE INVENTION

The method of the present invention treats individuals exhibiting symptoms associated with vascular headaches, including migraine headaches, by the administration of a therapeutically effective amount of a combination of calcium and vitamin D. Preferably, the dosage of elemental calcium administered is in the range of from about 600 mg to about 3000 mg per day. Preferably, the dosage of vitamin D administered is in the range of from about 400 to about 4000 IU per day or about 2800 to 50,000 IU weekly or even 50,000 to 200,000 IU weekly for individuals who are severely symptomatic or patients who need to be quickly loaded in order to normalize their 25 hydroxyvitamin D levels and then placed on maintenance. Preferably, the dosage of vitamin D elevates 25 hydroxyvitamin D levels to levels greater than 30-40 ng/ml. The calcium and vitamin D may be administered concurrently such as, for example, by administration of a tablet, a capsule, a powder, liquid, candy or mint, cookie, food additive or transdermal patch containing the desired dosages of the calcium and the vitamin D. Preferably, the combination is administered orally in the form of a tablet. Calcium may be administered in the form of, for example, calcium carbonate, calcium gluconate, calcium citrate, calcium phosphate, calcium chloride, calcium stearate or calcium acetate or any other calcium embodiment. The calcium may be administered orally, subliminally, parentally, rectally, or transdermally. Vitamin D may be administered as at least one of vitamin D2 (ergocalciferol), vitamin D3 (cholecalciferol) or 25 hydroxyvitamin D (calcidiol or calcifediol). The vitamin D may be administered orally or intramuscularly. The dose can be taken as a single daily combination dose or in split doses of smaller concentrations in adequate levels for prevention of migraine headaches- Examples of combinations for single doses are as follows:

| Elemental calcium | Vitamin $D_2$ or $D_3$ |
| --- | --- |
| 1000 mg | 400 IU |
| 1000 mg | 600 IU |
| 1000 mg | 800 IU |
| 1200 mg | 400 IU |
| 1200 mg | 600 IU |
| 1200 mg | 800 IU |
| 1200 mg | 1000 IU |
| 1200 mg | 1200 IU |
| 1200 mg | 2400 IU |
| 1500 mg | 400 IU |
| 1500 mg | 300 IU |
| 1500 mg | 800 IU |
| 1500 mg | 1000 IU |
| 1500 mg | 1200 IU |
| 1500 mg | 2000 IU |
| 1500 mg | 3000 IU |
| 2000 mg | 4000 IU |
| 2000 mg | 1000 IU |

Examples of smaller concentration embodiments to be administered at least 2 to 3 times daily are as follows:

| Elemental calcium | Vitamin $D_2$ or $D_3$ |
| --- | --- |
| 300 mg | 200 IU |
| 300 mg | 250 IU |
| 500 mg | 200 IU |
| 500 mg | 300 IU |
| 500 mg | 400 IU |
| 600 mg | 300 IU |
| 600 mg | 400 IU |
| 600 mg | 500 IU |
| 600 mg | 600 IU |
| 600 mg | 800 IU |
| 600 mg | 1000 IU |
| 600 mg | 1200 IU |
| 700 mg | 700 IU |
| 800 mg | 400 IU |
| 800 mg | 500 IU |
| 800 mg | 800 IU |
| 800 mg | 1200 IU |
| 1000 mg | 1000 IU |
| 1000 mg | 1500 IU |
| 1000 mg | 2000 IU |

The combination is effective for significantly reducing or relieving symptoms associated with migraine headaches, which include symptoms such as hemicranial, location pulsating pain, light or sound sensitivity, and nausea or vomiting.

The foregoing and other objects, features, aspects and advantages of the present invention will become more apparent from the following detailed non-limiting examples of the present invention.

Four patients sustained a marked improvement of their migraine headaches while receiving therapeutic replacement of vitamin D and calcium as detailed below.

EXAMPLE 1

A 33 year old black, right handed female from the Dominican Republic was referred for evaluation of frequent migraine headaches and PMS. She had a history of migraines since the age of six, and suffered from frequent migraine attacks at least 5 to times per month. She noted these headaches to be most severe in the premenstrual period, specifically within the first 2 to 3 days of menses. She complained of a recent increase in severity and frequency of migraines as well as worsening PMS. Her premenstrual symptoms of depression, irritability, breast swelling, leg and abdominal cramping increased in a crescendo pattern at least two weeks before the onset of menses, and subsided with menstruation. The headaches, on most occasions, were holocephalic and throbbing, accompanied by photosensitivity, phonophobia, nausea, often vomiting and were not heralded by an aura. Acetylsalicylic acid and acetaminophen were of little benefit during these attacks.

There was no history of major depression, psychiatric disturbance, thyroid disease, metabolic or rheumatologic disorders. She had a significant familial history of migraines with both her mother and sister experiencing similar headache attacks. Previous laboratory evaluation for an episode of uveitis included normal values of serum electrolytes, Lyme's titer <20 EU/ml, angiotensin 17.0 (8–52), thyroid function tests, serology for syphilis, HLA-B27, antinuclear antibody, and a negative culture for Herpes Simplex virus. The erythrocyte sedimentation rate was 30. Chest x-ray demonstrated a normal cardiac silhouette without evidence of infiltrates or effusions.

General physical examination was normal. Repeat complete blood cell count, serum electrolytes, and uric acid were reported as within normal limits. A 25 hydroxyvitamin D level (25OHD) was obtained and reported as <5.0 ng/ml (16–74), the intact parathyroid hormone level 64 pg/ml (10–65), the serum calcium 9.2 mg/dl (8.5–11.0), the serum phosphorus 3.4 mg/dl (2.4–4.7) and the serum magnesium 2.4 mg/dl (1.5–2.5). She was initially treated with combination Cholecalciferol 1600 international units and elemental calcium 1200 mg per day. Within 2 months, migraine headache attacks were dramatically reduced along with her premenstrual symptomatology. A repeat 25OHD level following this therapy was 17.3 ng/ml.

Treatment with a higher dose of oral vitamin D2 at 50,000 units weekly, resulted in elimination of her PMS symptoms, and further amelioration in the frequency of her migraine attacks. At this therapeutic dosage of vitamin D2, a 25OHD level was reported at 41.8 ng/ml.

EXAMPLE 2

A 40 year old, right handed, Hispanic female had a history of migraines with aura since adolescence and a 10 year history of PMS. She regularly suffered at least 4 headache attacks per month, with each attack lasting 1–3 days. During these attacks, she was incapacitated and unable to go to work during the day or attend night classes. Her typical migraines would be preceded by a transient episode of scintillating scotomata and visual disturbances, followed by a severe, throbbing hemicranial headache. The headaches were often accompanied by intense nausea and vomiting, photophobia and paresthesias of her face. As a child, an EEG had been normal. Her mother had a similar frequency and pattern of migraine attacks. Over the years, she had been treated with elavil, librium, caffeine tablets, and propranolol with only partial success. Recently, a significant proportion of headache attacks were occurring during the premenstrual period accompanied by severe premenstrual symptomatology. General physical examination was normal with the exception of mild hypertension. Complete blood count, serum electrolytes, thyroid function tests, serology for syphilis were normal. Total serum calcium was 9.6 mg/dl (8.8–10.4), 25OHD was 17 ng/ml (9–52), and intact parathyroid hormone was 46 pg/ml (10–65).

Treatment of her premenstrual symptomatology with Cholecalciferol 1200 international units combined with elemental calcium 1200 mg daily for 3 months, resulted in a significant reduction of her migraine headaches as well as PMS symptoms. A 25 hydroxyvitamin D level following therapy was 42 ng/ml. Further migraine attacks were aborted by immediately ingesting and chewing the equivalent of 1200 to 1600 mg of elemental calcium.

EXAMPLE 3

A 65 year old, postmenopausal, right-handed, Hispanic female was referred for frequent migraine headaches following an earlier stroke provoked by an intractable migrainous attack. She had a previous 30 year history of occasional migraines without aura accompanied by nausea, vomiting and photophobia. In 1990, she underwent surgical clipping of an anterior communicating artery aneurysm for a subarachnoid hemorrhage, and noticed a dramatic increase in frequency and duration of her migraine headaches. One year following the surgery, she was experiencing weekly migraines lasting for days. A cranial CT scan in 1991 revealed low attenuation throughout the left frontal lobe consistent with postoperative focal encephalomalacia. The third and lateral ventricles were mildly prominent; there was no hydrocephalus or midline shift. Three years following surgery, migraines were occurring at least three times a week. She was referred for medical evaluation.

Her headaches were described as holocephalic accompanied by nausea, vomiting, photophobia and noise irritability. They were excruciating, recurrent, and now occurring daily. She denied paresthesias or any lateralizing sensorimotor complaints. There was no weight loss, seizures, incontinence, diplopia. She had no history of any other major medical problem as diabetes mellitus, hypertension, cardiac, pulmonary or rheumatological diseases. There was a familial history of migraines.

General physical examination was normal. She was alert and oriented with fluent speech. Cranial nerves were symmetrical; sensory and motor examination were normal. There was no drift, tremor, ataxia, or gait disturbances. Repeat cranial CT scan in 1994 demonstrated a left frontal craniotomy with aneurysm clippings. The fourth ventricle was midline. There was no significant ventriculomegaly, except for exvacuo dilatation of the left frontal horn. Comparison of the scan with the previous study revealed no evidence of an interval change. Complete blood count, platelet count, ESR, urea, electrolytes, total calcium, magnesium, uric acid, thyroid function, latex fixation, and syphilis serology were normal. A 25 hydroxyvitamin D level was 15 ng/ml (16–74), an intact parathyroid level 25 pg/ml (10–65), a 1,25 dihydroxyvitamin D level 122 pg/ml (30–75). She was initially prescribed propranolol with a reduction of her migraines, but with a return of her daily migraine pattern, was discontinued from this regimen. Therapeutic replacement with vitamin D2 in a dose of 50,000 units weekly combined with oral elemental calcium titrated to a dose of 2000 mg daily resulted in a dramatic reduction in her migraine headaches without rebound of her symptoms. A repeat 25 hydroxyvitamin D level following therapy was 52 ng/ml and a 1,25 dihydroxyvitamin D level was 59 pg/ml.

EXAMPLE 4

A 50 year old postmenopausal, black female was referred for evaluation of frequent migraine headaches despite prophylactic therapy. She had a 5 year history of migraines with aura and noticed a significant increase in the number of headaches attacks since estrogen replacement therapy was prescribed following a total abdominal hysterectomy and bilateral salpingo-oophorectomy. Her typical migraine was preceded by bilateral visual disturbances and transient blindness erupting into an excruciating headache. Paresthesias of her right upper extremity would often spearhead, but sometimes accompany the onset of the headache. The migraine was characterized by a right hemicranial, pulsating headache accompanied by nausea, vomiting and right facial numbness. The usual frequency of her headache was 2 to 3 times a week. The duration of her headache varied from 4 hours to days. During the past year, she was prophylactically treated with a slow calcium channel blocker, diltiazem, combined with the antispasmodic agent, papaverine. (Both calcium channel blockers as well as papaverine have been used for the relief of cerebral and myocardial ischemia associated with arterial spasm.) However, this regimen failed to affect the frequency of her migraine attacks or reduce her usage of either ergotamine or sumatriptan. Cranial CT scan was normal in 1992.

There was a childhood history of asthma, and a history of mild hypertension which was controlled on a diuretic agent. There was no history of cardiac disease, thyroid disease, diabetes mellitus, rheumatological disorders or major depression.

General physical and neurological examination was normal. Laboratory evaluation which included a complete blood count, electrolytes, urea nitrogen, antinuclear antibody, double stranded DNA, thyroid functions were reported as within normal limits. The 25 hydroxyvitamin D was 19.8 ng/ml (16–74), total calcium 9.7 mg/dl (8.5–11.0), and intact parathyroid hormone 16 pg/ml (10–65). Although the 25 hydroxyvitamin D level was reported as normal by the commercial laboratory, some authorities suggest that 25 hydroxyvitamin D levels below 30 ng/ml are marginal and represent a subclinical deficiency. Heaney R., *Calcium, Bone Health and Osteoporosis In Bone and Mineral Research,* Elsevier Science Publishers., 1986, 255–301; Francis et al. "Calcium Malabsorption In The Elderly: The Effect of Treatment With Oral 25-hydroxyvitamin D3", *European J. Clin. Invest.,* 1983, 13:391–396.

The administration of vitamin D2 in a dose of 50,000 IU weekly combined with 1000 mg daily of elemental calcium dramatically reduced her migraine headache attacks. Maintenance of the 25OHD level above 40 ng/ml significantly decreased both the duration and frequency of headache attacks.

DISCUSSION OF THE RESULTS

Four examples of migraineurs are presented herein. Each met the diagnostic criteria of the International Headache Society for migraine headaches. In all four women, the reduction in frequency and duration of their migraine headaches was observed on therapeutic replacement with vitamin D and calcium.

The precise role vitamin D and calcium play in the pathogenesis of migraine is not known. And what interaction, if any, exists between calcium and the serotoninergic system in the pathophysiology of migraines is not clear. The Calcium ion serves important extracellular and intracellular functions in the regulation of muscle contraction and in neurohormonal secretions. At the cellular surface, calcium controls the permeability of cells and the excitability of nervous tissues. Within the cell, it controls metabolism. The importance of calcium in pre and post synaptic nerves and in the release of neurotransmitters has long been recognized. Small changes in calcium concentration in the cell cytosol can either promote or inhibit cellular responses. Bohr noted a dual effect of calcium on vascular smooth muscle, when he studied the contractile response of rabbit aorta. Bohr D., "Vascular Smooth Muscle: Dual Effect of Calcium", *Science,* 1663, 19:597–599.

In the present invention, an increase in calcium and vitamin D concentration resulted in membrane stabilization and an elimination in the threshold for excitation, while calcium and vitamin D levels below physiological levels increased excitability and labilized the membrane. The calcium ion, combined with vitamin D, may ultimately modulate intricate hormonal and physiological feedback mechanisms that control somatic responses.

Example 3 is of particular interest, because it describes a postmenopausal migraineur who developed frequent and excruciating migraine headaches following a hemorrhagic stroke. Both intracranial infarction and hemorrhage have been reported to occur in patients suffering refractory migraines. The pathogenesis of stroke in migraine has not been resolved, but it is believed that cerebral vasospasm (i.e., a spasm or constriction of the blood vessels) resulting in a reduction of blood flow and ultimately, ischemia is one of the causative mechanisms. Multiple case reports have described angiographic findings of diffuse and segmental intracranial arterial vasospasm in patients with migrainous infarctions. Others have proposed that the temporary ischemia of the vessel followed by reperfusion and then rupture of the vessel may explain the intracerebral hemorrhage. Alterations in this patient's cellular calcium homeostasis may have been instrumental in triggering the cerebral vasospasm in her migrainous headaches and in her stroke. Physiologic alterations in calcium and vitamin D in all four patients, may well have triggered the vasomotor instability and vasospasm clinically manifesting as migraines, while therapeutic vitamin D and calcium effected membrane stabilization and the alleviation of migraine symptoms.

The results of examples 1–4 demonstrate that combined vitamin D and calcium therapy has been observed to significantly reduce the frequency and duration of headache attacks in migraine sufferers.

I claim:

1. A method for treating a vascular headache comprising administering to an individual having symptoms associated with vascular headache symptomatology an amount of a combination of calcium and vitamin D effective to significantly reduce said symptoms.

2. The method of claim 1 wherein the vitamin D is administered in the form of ergocalciferol (D2), cholecalciferol (D3) or calcidiol.

3. The method of claim 1 wherein the calcium comprises elemental calcium administered in the form of calcium carbonate, calcium citrate, calcium gluconate, calcium lactate, calcium acetate, or calcium stearate.

4. The method of claim 1 wherein the calcium comprises elemental calcium administered in an oral dose in the range of from about 600 to 3000 mg daily.

5. The method of claim 1 wherein the vitamin D comprises vitamin D2 or D3 administered in an oral dose in the range of from about 400 to 4000 IU per day.

6. The method of claim 1 wherein the vitamin D comprises vitamin D2 or D3 administered in an oral dose in the range of from about 50,000 to 200,000 IU weekly.

7. The method of claim 1 wherein the vitamin D comprises vitamin D2 administered as an intramuscular dose of 100,000 to 500,000 IU in an oil base every $2 \geqq 3$ months.

8. The method of claim 1 wherein the calcium comprises elemental calcium administered as an oral, sublingual, parenteral or transdermal dose.

9. The method of claim 1 wherein the vitamin D is administered as an oral, sublingual, parenteral or transdermal dose.

10. The method of claim 1 wherein the calcium is administered in an amount of about 2000 mg per day and the vitamin D is administered in an amount of about 1000 IU per day.

11. The method of claim 1 wherein the calcium is administered in an amount of about 1200 mg per day and the vitamin D is administered in an amount of about 1200 IU per day.

12. The method of claim 1 wherein the calcium is administered in an amount of about 2000 mg per day and the vitamin D is administered in an amount of about 4000 IU per day.

13. The method of claim 1 wherein the calcium is administered in an amount of about 600 mg 2 to 3 times daily and the vitamin D is administered in an amount of about 600 IU 2 to 3 times daily.

14. The method of claim 1 wherein the calcium is administered in an amount of about 600 mg 2 to 3 times daily and the vitamin D is administered in an amount of about 1200 IU 2 to 3 times daily.

15. The method of claim 1 wherein the calcium is administered in an amount of about 800 mg 2 to 3 times daily and the vitamin D is administered in an amount of about 400 IU 2 to 3 times daily.

16. The method of claim 1 wherein the calcium and the vitamin D are administered in the form of a tablet, capsule, powder, liquid, candy, cookie, or transdermal patch.

17. The method of claim 1 wherein the vitamin D is administered in an amount effective to elevate the individual's 25 hydroxyvitamin D level to a level greater than 30–40 ng/ml.

18. A method for treating vasospasm comprising administering to an individual having symptoms associated with vasospasm an amount of a combination of calcium and vitamin D effective to significantly reduce the symptoms.

* * * * *